United States Patent [19]

Tranberg et al.

[11] Patent Number: 4,765,318
[45] Date of Patent: Aug. 23, 1988

[54] ORTHOPEDIC KNEE BRACE

[75] Inventors: Per Tranberg, Lerum, Sweden; Ralph Matties, Hamburg, Fed. Rep. of Germany; Dale Reese, Göteborg, Sweden

[73] Assignee: Volcano International Medical AB, Hisings Backa, Sweden

[21] Appl. No.: 6,196

[22] Filed: Jan. 23, 1987

[51] Int. Cl.4 .................................................. A61F 3/00
[52] U.S. Cl. .................................... 128/80 C; 128/165
[58] Field of Search .................... 128/80, 80 C, 80 H, 128/80 E, 80 F, 80 G, 80 A, 80 B, 80 D, 165

[56] References Cited

U.S. PATENT DOCUMENTS

| 2,858,540 | 11/1958 | Morrison | 128/80 C |
| 4,201,203 | 5/1980 | Applegate | 128/80 C |
| 4,370,978 | 2/1983 | Palumbo | 128/80 C |
| 4,445,505 | 5/1984 | Labour et al. | 128/80 C |

FOREIGN PATENT DOCUMENTS 2553996  5/1985  France .................. 128/80 C

Primary Examiner—Edgar S. Burr
Assistant Examiner—Huong Q. Pham
Attorney, Agent, or Firm—Wegner & Bretschneider

[57] ABSTRACT

An orthopedic knee brace formed as a tubular member made of a material having a core of foamed rubber material, which on both faces is laminated with textile fabric, is provided with an opening in the region intended to be located above the patella of the wearer. Primary Velcro-type fastener segments are attached to the tubular member, to each side of the opening, and oriented along two separate lines, substantially in parallel with the longitudinal axis of the member. The segments are adapted to form attachments for at least one secondary Velcro-type fastener strip, separable from the member and having a length substantially equal to the distance between the outward edges of the outer, primary Velcro-type fastener segments.

3 Claims, 3 Drawing Sheets

FIG. 7
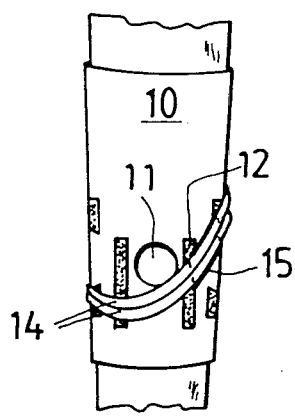
FIG. 8
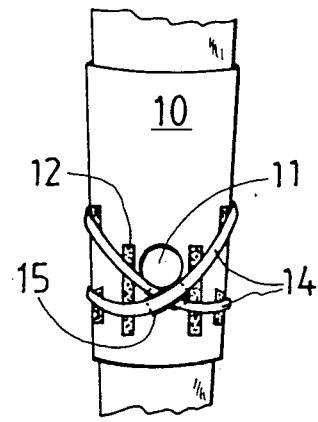
FIG. 9
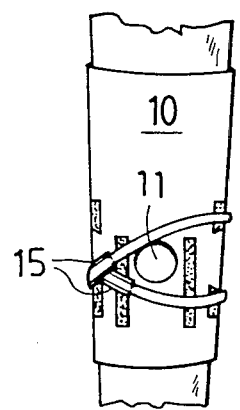
FIG. 10
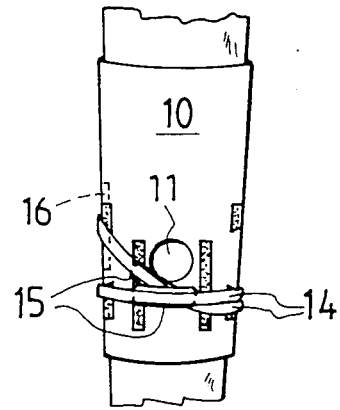
FIG. 11

ID BRACE

BACKGROUND OF THE INVENTION

The present invention refers to an orthopedic knee brace including a tubular member having a supporting core of foamed rubber material, which on both faces is laminated with a textile fabric, and is provided with an opening in the region intended to be located so as to at least cover the patella of the wearer.

Braces of this type are often used to prevent injuries of the knee joint and surrounding tissues as well as to promote the healing of damages in this region. Due to the special properties of the material used the protected region is stimulated by increased heat, promoting blood flow, which reduces the risk for injuries caused by cold stiffness and facilitates the healing of tissue injuries.

Many sports and occupational injuries will affect the knee joint, and will often appear as a stretching of joint and collateral tissues, which causes instability and pain when the knee is subjected to load. An instable knee will often encounter agravated damages, which means that a long rest is prescribed even for a slight injury. Tapes have been used to stabilize an injured knee. This method presupposes a high degree of orthopedic knowledge, and is therefore mostly used when preparing an elite sportsman for a contest. Knee corsages with articulated metal splints are also used, but those are rather clumsy, and are regarded as a hindrance during normal sport exercises or professional work.

SUMMARY OF THE INVENTION

The object of the present invention is to propose an orthopedic knee brace, which can be used for additional treatment of various types of inflammations and overloads at the knee joint for increasing the stability thereof and stimulating inflammed regions, and which can be worn without hindrance during normal sport exercises and working operations.

To that end the invention is characterized in segments of primary Velcro-type fasteners located to each side of the opening and oriented along two separate lines substantially in parallel with the longitudinal axis of the tubular member to form attachments for at least one secondary Velcro-type fastener strip, separable from the member, and having a length substantially equal to the distance between the outward edges of the outermost, primary Velcro-type fastener segments.

Preferably outer primary segments are twice as broad as inner primary segments.

According to an advantageous embodiment of the invention a secondary strip is provided with a fixed pad having a length exceeding the transverse measure of the opening.

A secondary strip is preferably made of resilient material and includes two end parts extending in opposite directions from its pad.

The inner primary fasteners preferably are strips extending from about the level of the top of the opening to a distance well below the lower margin thereof, whereas the outer primary fasteners each including two separate patches located respectively above and below the opening. The outer paches are advantageously formed so their juxtaposed edges slant away from the opening.

BRIEF DESCRIPTION OF THE DRAWINGS

FIGS. 5–10 show different manners of using the brace, and FIG. 11 shows a separate pad.

DESCRIPTION

Figure 1:
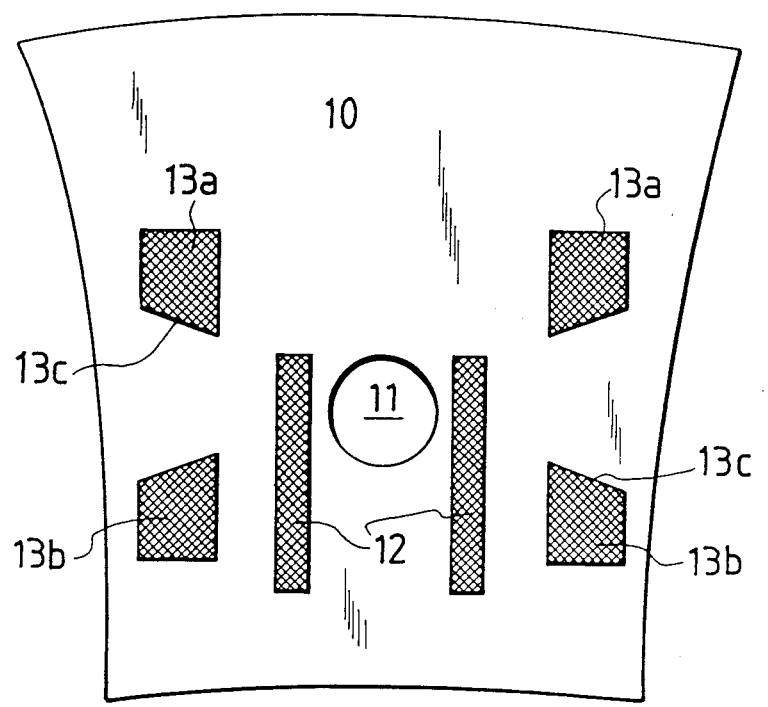
FIG. 1 is a plan view showing a flattened-out blank for a knee brace according to the invention.
Figure 2:
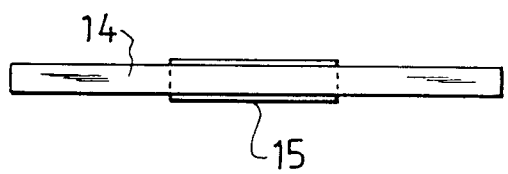
FIG. 2 is a plan view of a secondary strip provided with a pad.
Figure 3:
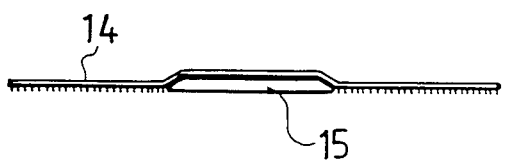
FIG. 3 is a side view of the strip shown in FIG. 2.
Figure 4:
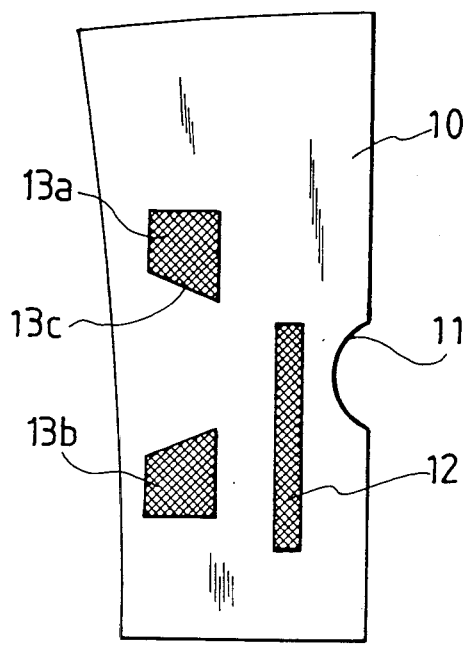
FIG. 4 shows a side view of the blank according to FIG. 1 formed into a tubular member.

The knee brace according to the invention is formed as a slightly tapering tubular member 10 with a core of foamed rubber material which on both faces is laminated with textile fabric. An opening 11 is located at about the middle portion of the member, the opening being intended to be located at the patella of the wearer.

Two separate lines of Velcro-type fastener segments 12, 13 are located to each side of the opening 11 of which the outer segments 13 are at least twice as broad as the inner segments 12. The segments run substantially parallel to the longitudinal axis of the tubular member, and belong to a primary component of this type of fastener, i.e. either the male, or the female half of the fastener.

The primary segments 12 and 13 may be formed as strips, but in order that the brace shall offer small resistance to the bending of the knee, the location, and the form, especially of the outer segments is important.

The inner, narrow primary segments 12 are strips extending from about the level of the top of the opening 11, to a distance well below the lower margin thereof, say about corresponding to the diameter of the opening.

The outer, broader segments each includes two separate patches 13a, 13b located above and below the opening 11 respectively. The juxtaposed edges 13c of these patches slant in the direction away from the opening. The pointed end of the lower patch 13b is located about level with the lower margin of the opening 11, whereas the pointed end of the upper patch 13a is located somewhat above the upper margin of the opening.

These primary segments are intended to co-operate with secondary Velcro-type fastener strips 14 of the opposite type, i.e. either the female or the male half. Each secondary strip 14 is at its middle portion provided with an elongate pad 15.

Figure 5:
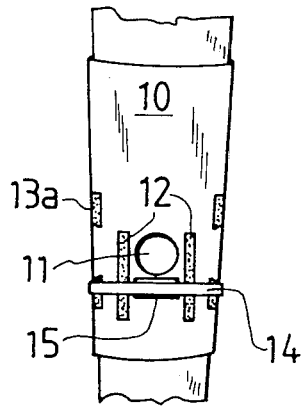

FIG. 5 shows the use of a padded Velcro-type strip 14 located immediately below the opening 11. This location at the lower edge of the patella promotes the healing of a so called jumpers knee, or a knee suffering from "Osgood-Schlatter" disease. With graver cases of those damages two crossing strips 14 may be located diagonally below the patella, as shown in FIG. 8.

Figure 6:
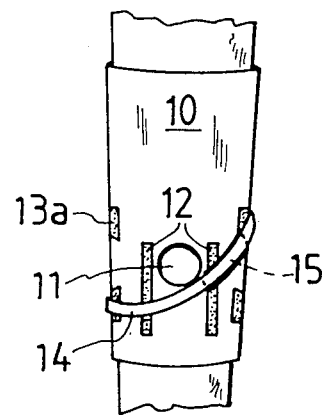

FIG. 6 shows a strip 14 located somewhat diagonally with the pad 15 at the inward side of the patella, which offers a support for medial collateral ligaments. FIG. 7 shows a modification where two strips 14 are used in parallel for correcting of an injury in this region.

FIG. 9 shows two strips 14 located so as to cross each other, diagonally at the outside of the patella, and with their pads 15 supporting the edge of the patella. In this manner the patella will obtain a support during "patellae luxation", i.e. the patella has suffered from an out of joint laterally.

FIG. 10 shows a further manner of use with one diagonal and one horizontal strip 14, crossing each other below the patella. This is used for treating "chondomalacia patellae" and lateral displacement of the patella.

The fields of use for the knee brace described above are examples only for ways of preventing and treating various knee joint problems. Among other fields of use the prevention of ventral weakness after collateral ligament damage may be mentioned, as well as bilateral support for treating lateral and medial collateral ligament, during laterization of the patella.

Further variations and certain treatment methods are possible, depending upon the degree of injury, simply by increasing the number of padded secondary strips, and their location in relation to the knee joint. A female half of a Velcro-type fastener is resilient, so the strip may be stretched, before it is applied, whereby the tensioning force of the strip, across the knee joint, will be increased The location of a pad 16 shown in FIG. 11 is indicated in broken lines in FIG. 10, when introduced between the tubular member 10 and the skin of the wearer. The pad is provided with the male part of a Velcro-type fastener at its face to be turned towards the sleeve. Such a pad 16 may be used for increased stimulus at an injuried portion of the knee, and may be attached at arbitrary portion of the internal face of the tubular member.

As the brace will be centered by means of the opening 11 in relation to the patella, a brace with secondary strips applied by an orthopedic specialist may be removed and washed as a unit, and then be re-applied, without the secondary strips, being active for the treatment, having to be applied again by said specialist.

The invention is not limited to the embodiment above described, as many modifications are possible within the scope of the appended claims. Secondary strips 14 lacking pads 15 may for instance be used.

We claim:

1. A knee brace comprising a tubular member formed from a sheet having a core of foamed rubber material laminated on the inner and outer faces of said sheet with a textile fabric, and provided with an opening in a region of the member intended at least partly to be located above the patella of the wearer, and provided at said outer face with segments of inner and outer primary Velcro-type fasteners located in inner and outer spaced-apart lines, respectively, to each side of said opening, said lines being oriented substantially parallel with the longitudinal axis of said tubular member to form attachments for at least one secondary Velcro-type fastener strip, separable from said tubular member, and said at least one secondary fastener strip having a length at least sufficient to reach from one outer primary fastener to the other primary outer fastener, wherein said inner primary fasteners being strips extending from about the level of the top of said opening to a distance well below the lower margin thereof, wherein said outer primary fasteners, each being at least two separate patches located respectively above and below said opening.

2. A knee brace according to claim 1, in which said outer primary segments are broader, preferably twice as broad as said inner primary segments.

3. A knee brace according to claim 1, in which said outer patches having juxtaposed edges are formed so said juxtaposed edges slant away from said opening.

* * * * *